United States Patent
Overstreet et al.

(10) Patent No.: US 7,277,759 B2
(45) Date of Patent: Oct. 2, 2007

(54) METHOD OF RAPID NEURAL RESPONSE MEASUREMENT WITHOUT AMPLITUDE ATTENUATION

(75) Inventors: Edward H Overstreet, Valencia, CA (US); Guillermo A Calle, Simi Valley, CA (US); Kevin H Hood, Simi Valley, CA (US)

(73) Assignee: Advanced Bionics Corporation, Valenica, CA (US)

( * ) Notice: Subject to any disclaimer, the term of this patent is extended or adjusted under 35 U.S.C. 154(b) by 602 days.

(21) Appl. No.: 10/771,819

(22) Filed: Feb. 4, 2004

(65) Prior Publication Data
US 2004/0158170 A1  Aug. 12, 2004

Related U.S. Application Data

(60) Provisional application No. 60/444,985, filed on Feb. 4, 2003.

(51) Int. Cl.
*A61N 1/00* (2006.01)
(52) U.S. Cl. ........................................ 607/56; 607/137
(58) Field of Classification Search ................ 600/554, 600/559; 607/55–57
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 5,381,512 A | 1/1995 | Holton et al. | |
| 5,824,022 A | 10/1998 | Zilberman et al. | |
| 6,052,624 A | 4/2000 | Mann | |
| 6,393,325 B1 | 5/2002 | Mann et al. | |
| 6,751,505 B1 * | 6/2004 | Van Den Honert et al. | ... 607/57 |
| 6,915,166 B1 * | 7/2005 | Stecker et al. | ................ 607/55 |

* cited by examiner

*Primary Examiner*—Carl Layno
*Assistant Examiner*—Brian T. Gedeon
(74) *Attorney, Agent, or Firm*—Philip H. Lee; Victoria A. Poissant

(57) ABSTRACT

A method of recording neural responses reduces the inaccuracy of the recordings caused by nerve adaptation to repeated exposure of stimuli. In one embodiment, a maximum set of X number of successive stimuli are delivered through an electrode and the resulting neural response recorded and, afterwards, the next stimulation must occur through another electrode. This stimulation sequence prevents the same set of nerves from being stimulated too often, which can result in stimulus adaptation and cause measurement inaccuracy. In one embodiment of the invention, a smart software can be employed to provide visual plots of "growth curves", including real-time calculated datapoints and their confidence intervals, and automatically terminate the recording session upon reaching a pre-set trigger. Alternatively, a human operator can terminate a recording session, based on visual feedback of growth curves, including their real-time calculated datapoints and confidence intervals.

33 Claims, 11 Drawing Sheets

METHOD OF RAPID NEURAL RESPONSE MEASUREMENT WITHOUT AMPLITUDE ATTENUATION

The present application claims the benefit of U.S. Provisional Patent Application Ser. No. 60/444,985, filed 04 Feb. 2003, which application is herein incorporated by reference in its entirety.

BACKGROUND OF THE INVENTION

The present invention relates to methods of recording a neural response from neural tissue after it is stimulated. More specifically, the present invention relates to methods for rapidly and accurately recording and processing neural responses.

Modern neural stimulators have the capability of measuring the response of nerve tissue to an electrical stimulus. This involves delivering a stimulus to a nerve through a stimulating electrode and recording, with a sense or recording electrode, the electrical response of the nerve as it depolarizes and repolarizes.

Obtaining a neural response ("NR") for a particular electrode configuration and thus a particular set of nerves is important clinically to ascertain whether the targeted nerves are, in fact, being stimulated by the implanted stimulator system. It is further important to determine the range of stimulus amplitudes for which the nerve responds. Such nerve response information is used to set the stimulus parameters delivered by an implanted device such as a cochlear stimulator for the deaf. Another application where NR information could be used to help set stimulation parameters is spinal cord stimulation for treating chronic intractable pain. The use of cochlear and spinal cord stimulation systems are well-accepted medical therapies.

Conventional methods for determining NR involve obtaining multiple recordings of neural responses at a particular stimulus amplitude. The multiple recordings are then averaged to provide a more accurate, peak amplitude response. The averaged peaks are then plotted as a function of varying stimulus amplitudes for each electrode configuration. Such a resulting neural response curve is called an "input/output function" or, alternatively, a "growth curve" for a set of nerves stimulated by a particular electrode configuration.

Disadvantageously, the conventional methods of recording NRs often stimulate the same nerve repeatedly over a short duration of time in order to obtain an averaged response. The higher the stimulation frequencies, the more the NR appears to "adapt" resulting in an attenuation of the NR amplitude and thereby introducing inaccuracy in the NR recordings. In addition, the entire recording session often takes too long to complete in the clinical setting because the recordings to characterize the electrode configurations are performed inefficiently.

Accordingly, what is needed is a method for quickly recording and processing NRs, while eliminating inaccuracy caused by adaptation by a target nerve to repeated stimulation.

SUMMARY OF THE INVENTION

The present invention provides a method of recording and processing NRs which reduces the disadvantages presented above.

The method uses a system having an array of electrodes, E1 . . . EN, to generate growth curves, NR #1 to NR #Last, for each electrode configuration. The number of total electrodes, N, does not necessarily correspond to the number of electrode configurations or to the total desired number of neural response curves sought. More or less electrode configurations may be possible than the number of electrodes E1 . . . EN present.

In one embodiment, the method comprises: (a) delivering, without causing a predetermined level of NR attenuation, a stimulus train having X stimuli through one electrode of the array E1 . . . EN and recording, X number of times, a first NR datapoint, which datapoint is part of growth curve NR #1; (b) repeating the above process of stimulating through each selected ones of electrodes of the array E1 . . . EN and recording a datapoint corresponding to each selected electrode and each growth curve, NR#2 to NR #Last, wherein each datapoint is recorded at least once, without causing a predetermined level of NR attenuation; and (c) repeating the above steps (a) and (b) as many times as necessary to generate additional, different datapoints on each selected growth curve NR#1 to NR #Last; and wherein X is a variable, whole number 1 or greater, and X represents the number of stimuli in any stimulus train. Obviously, in the special case where X is 1, the "stimulus train" is composed of a single pulse and a recording for a datapoint is made only once. As used herein, the term "stimulus train" will be inclusive of the case where the stimulus train consists of only one stimulus pulse.

In another embodiment of the present invention a method is provided for obtaining neural responses to generate at least two growth curves with a stimulation system having an array of stimulating electrodes, E1 . . . EN. The method comprises: (a) delivering a stimulus train having X stimuli, without causing a predetermined level of attenuation of NR, the stimulus train delivered through a selected first electrode in the electrode array E1 . . . EN, to generate a replication of a data point for the first growth curve selected among, NR #1 . . . NR #Last; and (b) repeating step (a) for at least a second, selected electrode in the electrode array to generate a replication of a datapoint located on at least a second growth curve selected among, NR#1 . . . NR # Last, wherein delivering a first stimulus train to obtain a first datapoint and delivering a second stimulus train to obtain a second datapoint, when the two datapoints are located on the same, first growth curve, are never performed immediately one after the other, without the occurrence of an intervening wait state or an intervening delivery of a third stimulus to obtain a datapoint on a different, second growth curve; and wherein X is a variable, whole number 1 or greater.

The present method can prevent over-stimulation of any set of nerves and reduce the effect of response adaptation and thereby improve the accuracy of recording neural response growth curves.

In addition, one embodiment of the invention provides a software program that calculates real-time, averaged values of a replicated datapoint, its confidence intervals, and growth curve fitted through the available datapoints. By "replicated" it is meant multiple recordings of the same NR datapoint produced by applying a train of stimuli, wherein, usually, each stimulus in the train is the same. These data may be visually displayed in a real-time plot on a computer screen or other display means. In one embodiment, a software program can evaluate the real-time averages of every datapoint, its confidence interval and fit a resulting growth curve. If the program detects that the confidence level of a particular datapoint is not appreciably improving after a certain number of recordings or runs, then the recording of that particular datapoint will be terminated automatically by the software program, based on pre-programmed triggers or threshold values of changes in the confidence levels. In addition, the program can detect changes in the growth curve fitted to the available averaged datapoints. Based on pre-programmed triggers, when only a sufficiently small movement occurs in the growth curve as more datapoints are taken, the program can automatically terminate recording of a datapoint or even the remainder of a recording session. Alternatively, the operator may manually discontinue the recording of a particular datapoint or recording session when no appreciable changes are visually seen in the displayed confidence levels of the real-time calculated datapoint. Further, the operator may discontinue the recording session if there is no discernable visual movement in the real-time calculated and plotted growth curve.

It is a feature of the present invention to provide a recording and processing method that reduces inaccuracies introduced by nerve adaptation to exposure to repeated stimuli.

It is a further feature to provide a recording and processing method that can be terminated early in a recording session when further recording of data provides only a small improvement to the accuracy. The early termination thereby reduces the total time needed to conduct a full recording session.

BRIEF DESCRIPTION OF THE DRAWINGS

The above and other aspects, features and advantages of the present invention will be more apparent from the following more particular description thereof, presented in conjunction with the following drawings, wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
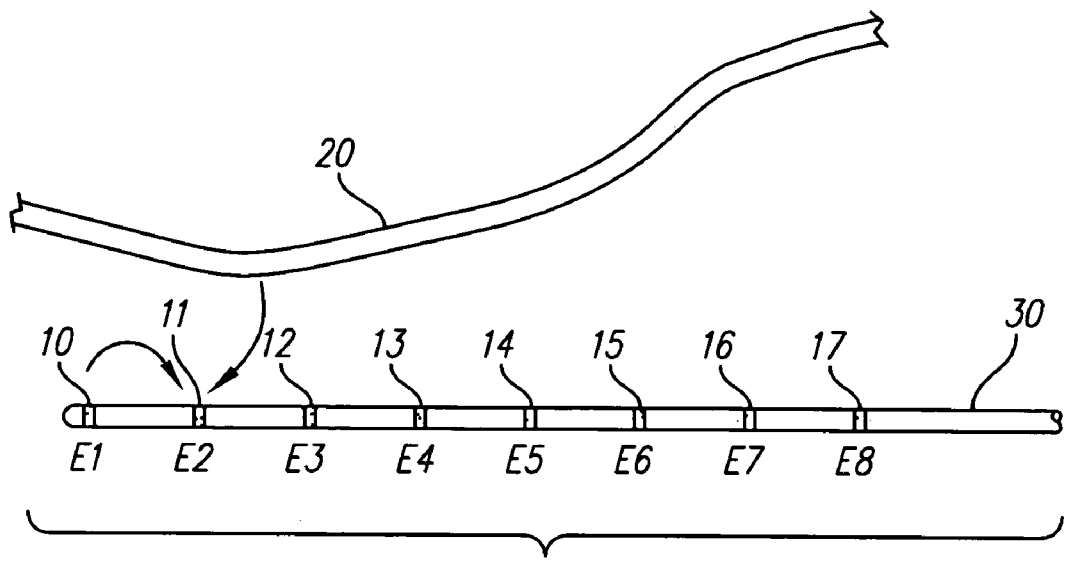
FIG. 1A shows an electrode array consisting of eight electrodes, E1 . . . E8, that may be used to stimulate a target nerve and optionally record a neural response.

FIG. 1A shows a lead 30 having an electrode array with electrodes E1 . . . E8, which are numbered 10-17. The lead 30 can be attached to an implantable pulse stimulator or generator ("IPG") (not shown). The IPG may provide independently controllable stimuli to each of the electrodes, 10-17. "Independently controllable," means that the stimulus provided through each electrode may be programmed for different stimulus parameters, e.g., pulsewidth, amplitude and frequency of stimulation for a train of stimulus pulses. In addition, in one embodiment, the circuitry in the IPG that is attached to each electrode E1 . . . E8 can be configured to allow switching between stimulation mode and recording mode, so that any electrode may function as a stimulating electrode or a recording electrode. As one example, electrode 10 may be selected as a stimulating electrode completing the stimulation circuit through the IPG housing which serves as a return or indifferent electrode. Such a stimulating electrode configuration is termed a "monopolar" stimulating electrode configuration. In one embodiment, electrode 11 (E2) may be selected as a recording electrode which forms a part of the recording circuit. Electrode 11 can record electrical activity along nerve 20. Alternatively the recording electrode may be placed on a separate lead, other than the lead 30 shown in FIG. 1A.

A representative cochlear stimulation system which utilizes electrode arrays and a cochlear stimulator is disclosed in U.S. Pat. No. 5,824,022, herein incorporated by reference in its entirety. Representative spinal cord stimulation systems utilizing electrode arrays to stimulate spinal cord nerves are disclosed in U.S. Pat. Nos. 3,646,940 and 3,724,467, which patents are herein incorporated by reference in their entireties.

Figure 1B:
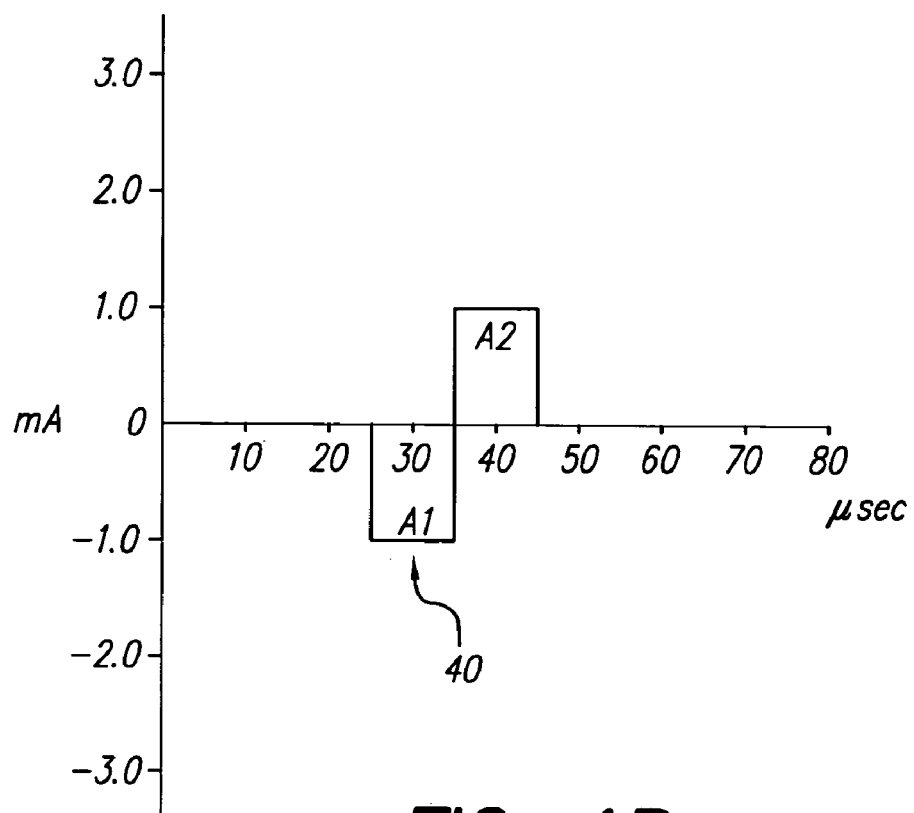
FIG. 1B shows an idealized, charged-balanced, biphasic, stimulus pulse that can be used to stimulate a nerve.

FIG. 1B shows one example of an idealized, biphasic stimulus that may be delivered through an electrode, e.g., electrode 10 (E1). The stimulus 40 can consist of two parts, a negative, first phase having area A1 and a positive, second phase having area A2. The stimulus has parameters such as an amplitude (mA) and a pulsewidth (microseconds). The pulsewidth in a biphasic stimulus is the first pulsewidth represented by the negative, first phase.

It is usually the negative or first phase that causes nerve tissue to depolarize (fire). The stimulus 40 shown is "charged balanced" because the negative area within curve A1 is equal to the positive area A2. Because the depolarization of nerve is initiated only by the negative phase of a stimulus, it is only necessary to have a uniphasic, cathodic pulse to effect nerve stimulation. Nevertheless, a biphasic, charge-balanced stimulus is often employed because such charge balancing helps reduce electrode corrosion and the build-up of charges which can harm surrounding tissue.

When the amplitude (mA) and pulsewidth (μsec) of the stimulus 40 is supra-threshold, i.e., large enough to depolarize or "capture" a target nerve, the voltage gradient at some surface point on the nerve 20 will be sufficiently negative as to cause the nerve to depolarize from its resting state and propagate an electrical signal along the length of the nerve. The voltage gradient of this electrical signal propagation can be captured using a recording electrode, for example, electrode 11 functioning as a recording electrode. The recorded NR is termed a "compound or massed action potential" of a nerve or a set of nerves.

Figure 1C:
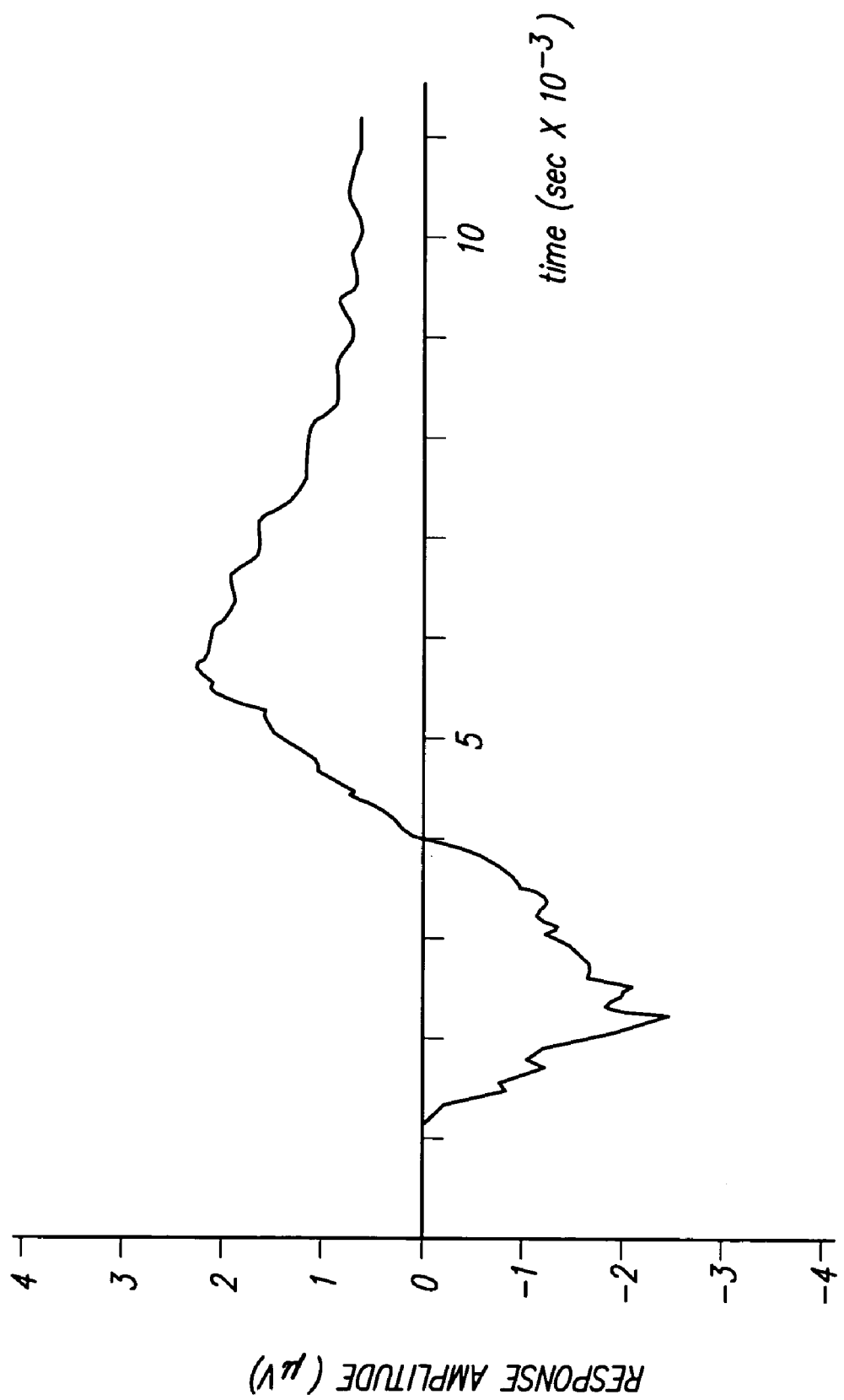
FIG. 1C shows a representative NR recording (compound action potential of many nerve fibers)

FIG. 1C depicts a representative illustration of an NR using a recording sampling rate that may range from about $10^5$ to $10^6$ Hz. In the cochlear field, the peak (sensed) amplitudes of the extracellular recorded NRs are generally in the millivolt or even microvolt range. In general, the action potential of the set of nerves is often obscured by the stimulus artifact which must be subtracted out by various known processing and recording methods such as forward masking. Thus, to obtain a single recording of an NR which represents the neural response or the action potential of a nerve, it is usually necessary to obtain many recordings. The NR represents the summed response (compound action potentials) of at least a few nerve fibers and, more typically, hundreds of nerve fibers. A single such recording of a cochlear nerve NR (an action potential) is generally ragged. There is usually some variability in peak response from recording to recording and the variability further depends on the specific stimulating and recording system used. In order to obtain a more accurate measure of the "true" peak of an NR, it is necessary to obtain a multiple number of recordings of the NR at a given applied stimulus amplitude to calculate the average value of the response peak. Typically, in a clinical setting, between 32 to 128 recordings are made to determine the averaged value. The sampling rate for a single recording (recordings/sec) may conventionally be between about 30 to 500 Hz.

The peak value of the NR that is obtained in response to a specific stimulus will be referred to as a "datapoint" on a NR growth curve for a particular electrode or electrode configuration. More datapoints on a particular growth curve can be obtained by varying the applied stimulus magnitude. The magnitude of the stimulus can be varied by changing either the amplitude (milliamperes) or the pulsewidth (microseconds). Generally, each particular NR datapoint resulting from an applied stimulus amplitude must be recorded multiple times in order to obtain an accurate average. Once all the recordings are averaged, the NR peak of each datapoint may be determined by a software program that determines the peak of the averaged NR. After all the desired datapoints are averaged and calculated, they may be plotted on a graph where the X-axis represents the stimulus amplitude and the Y-axis represents the averaged peak of the NR. The curve fitted through the averaged datapoints is the so-called "growth curve".

The growth curve thus obtained provides a characteristic response of a particular electrode configuration stimulating a set of nerve fibers. Obtaining an accurate determination of the growth curve is important clinically in order to determine the range of stimulus amplitudes that should be applied for each electrode configuration which may represent one stimulation channel. It is important that the range of stimulus applied by the implantable stimulator corresponds to the response range of the nerves recruited by a particular electrode configuration in order that the entire response range of the nerves is fully utilized and also to prevent delivery of stimulus having too much energy which could harm the nerves.

Figure 2:
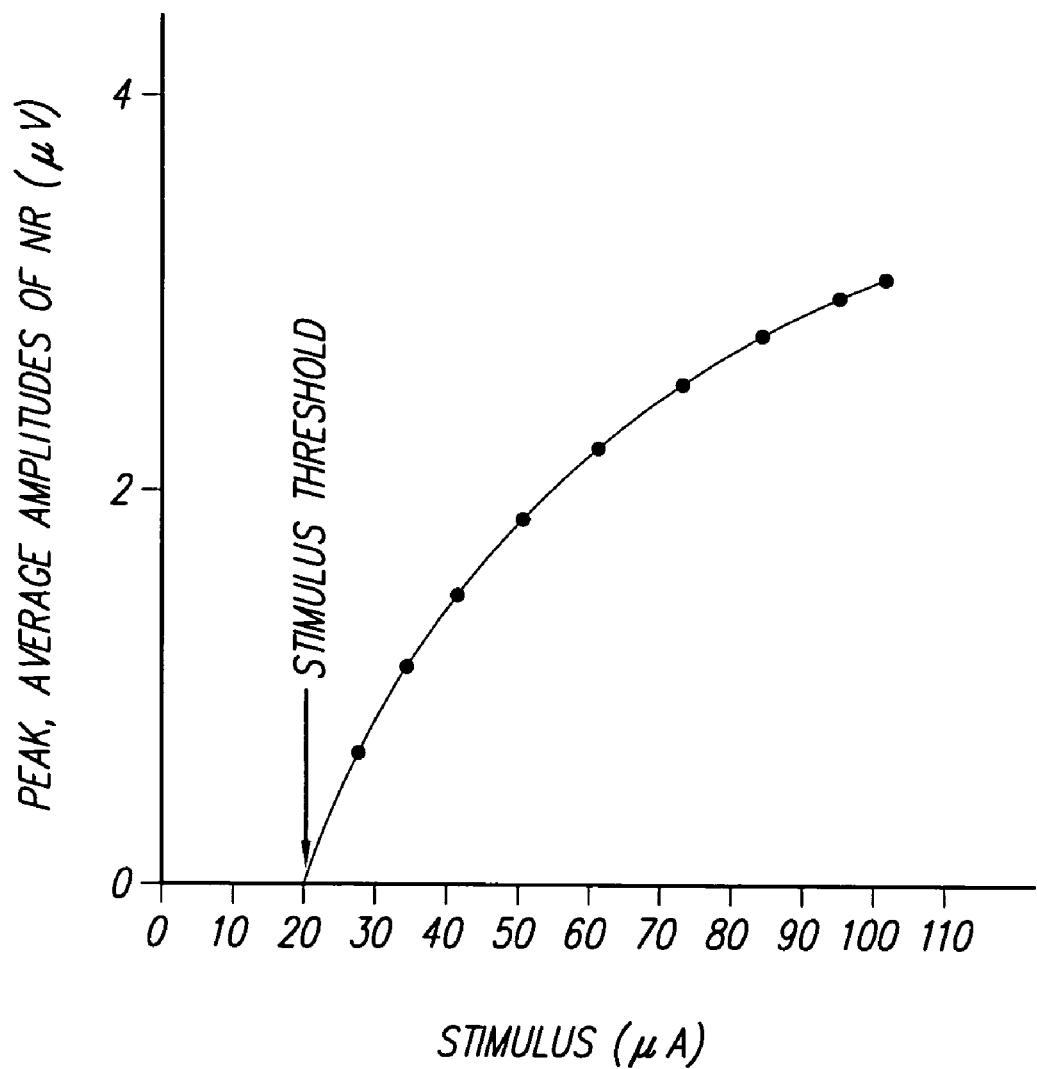
FIG. 2 shows a representative "growth curve" of a set of nerves stimulated by a particular electrode or electrode configuration, where the X-axis is the stimulus amplitude applied and the Y-axis is the peak response value of the NR.

FIG. 2 depicts a representative growth curve for a particular electrode or electrode configuration. The zero intercept at the X-axis of the growth curve represents the minimum "threshold" stimulus amplitude (microamperes) that must be applied in order to capture at least a few nerves or a set of nerves. In practice, the perception threshold for cochlear nerve stimulation is extremely fine. Individuals may be able to discern when only a few nerves are firing. The action potential produced by the few nerves firing usually cannot be detected because it is obscured by the inherent noise of the measuring system and thus cannot be captured with direct recordings. Instead, an indirect method is used to estimate the threshold stimulus (microamperes) of the electrode configuration. This is accomplished by curve-fitting the datapoints and generating a plot of the growth curve and extrapolating the X-zero intercept which represents the threshold stimulus amplitude.

Figure 3:
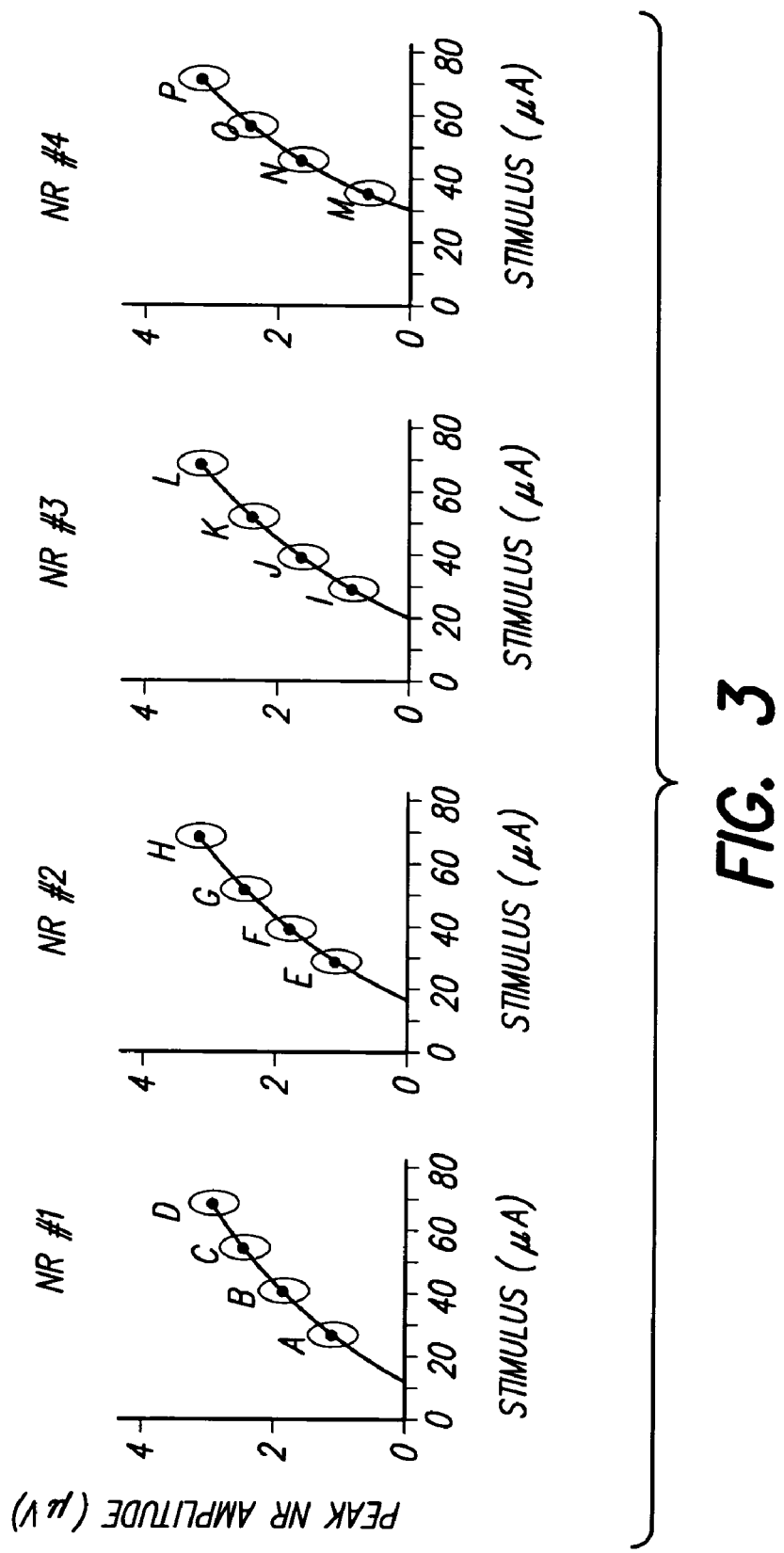
FIG. 3 shows, in accordance with the present invention, NR growth curves for four sets of nerves which are stimulated by four different electrodes or electrode configurations.
Figure 4:
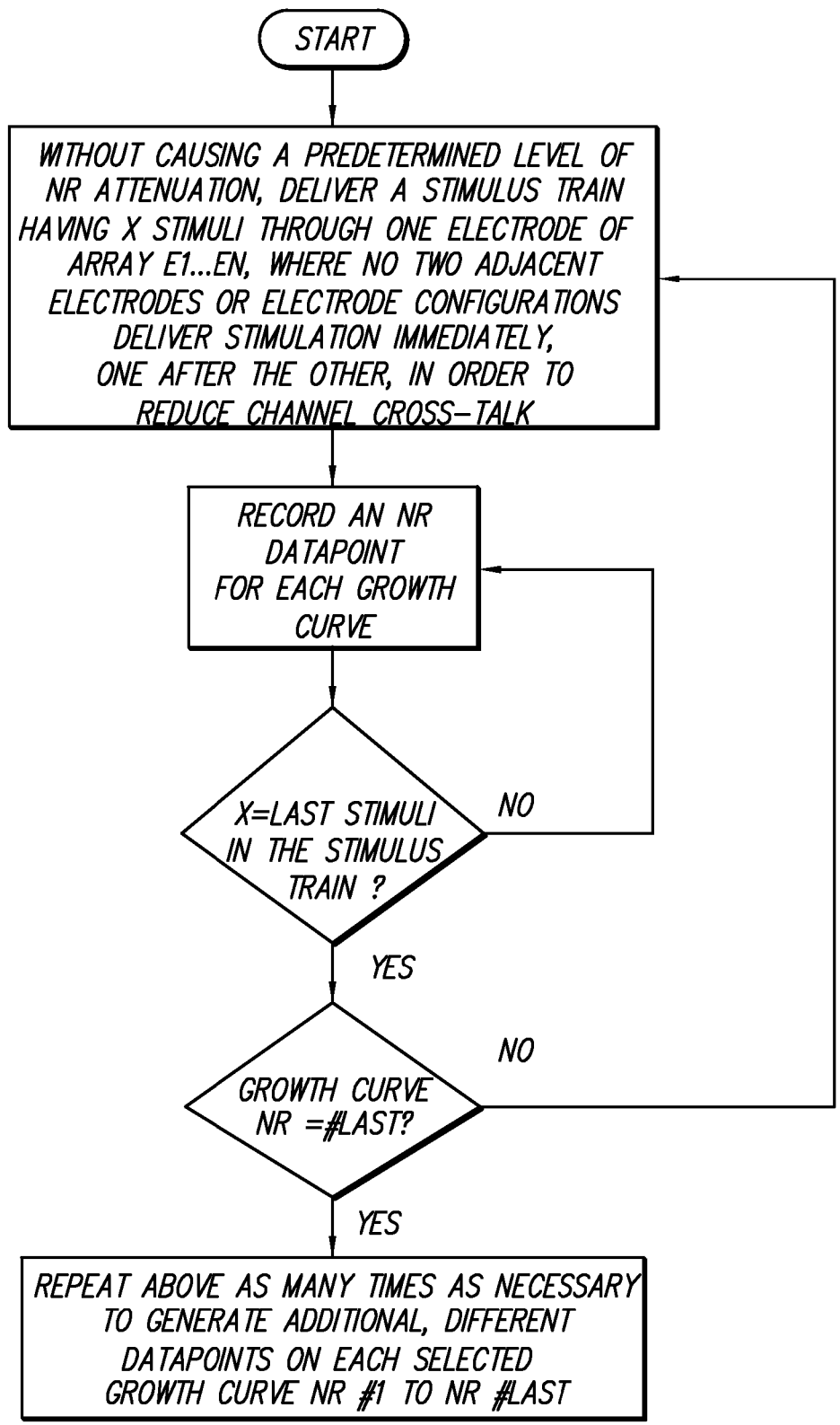
FIG. 4 is a first flow chart of an exemplary method of obtaining neural responses with a stimulation system having an array of electrodes, E1 . . . En, to generate growth curves.
Figure 5:
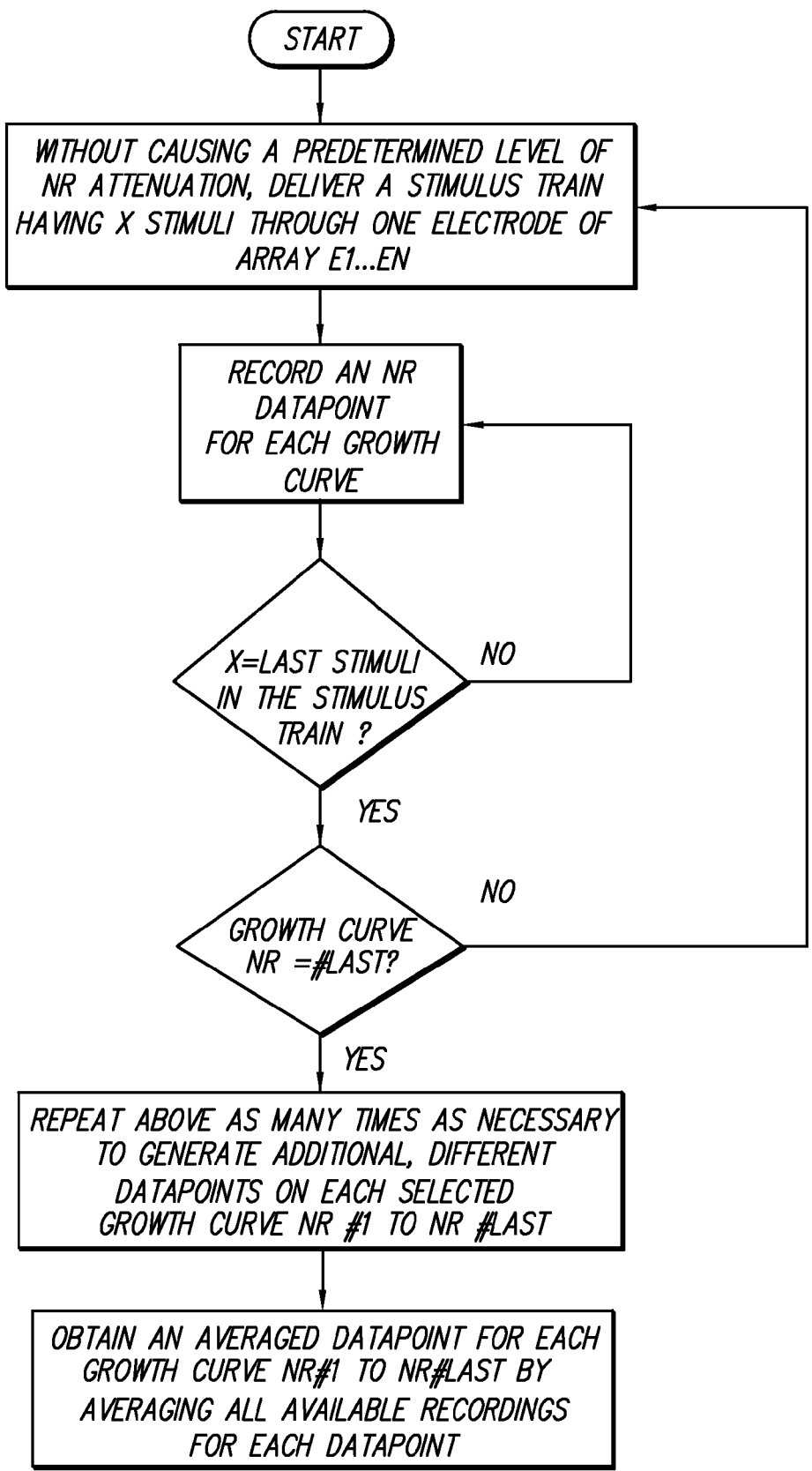
FIG. 5 is second flow chart of an exemplary method of obtaining neural responses with a stimulation system having an array of electrodes, E1 . . . En, to generate growth curves.
Figure 6:
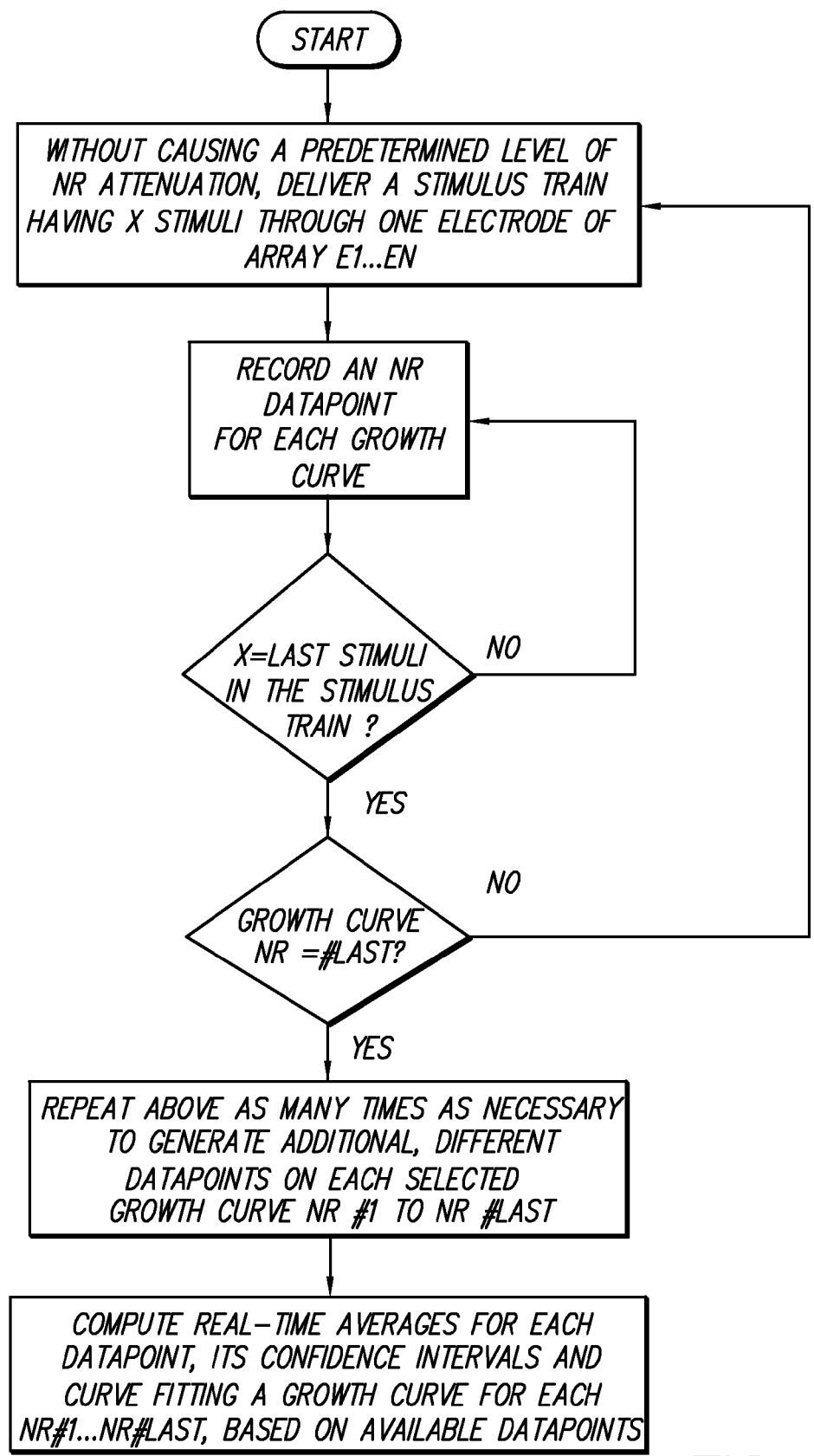
FIG. 6 is third flow chart of an exemplary method of obtaining neural responses with a stimulation system having an array of electrodes, E1 . . . En, to generate growth curves.
Figure 7:
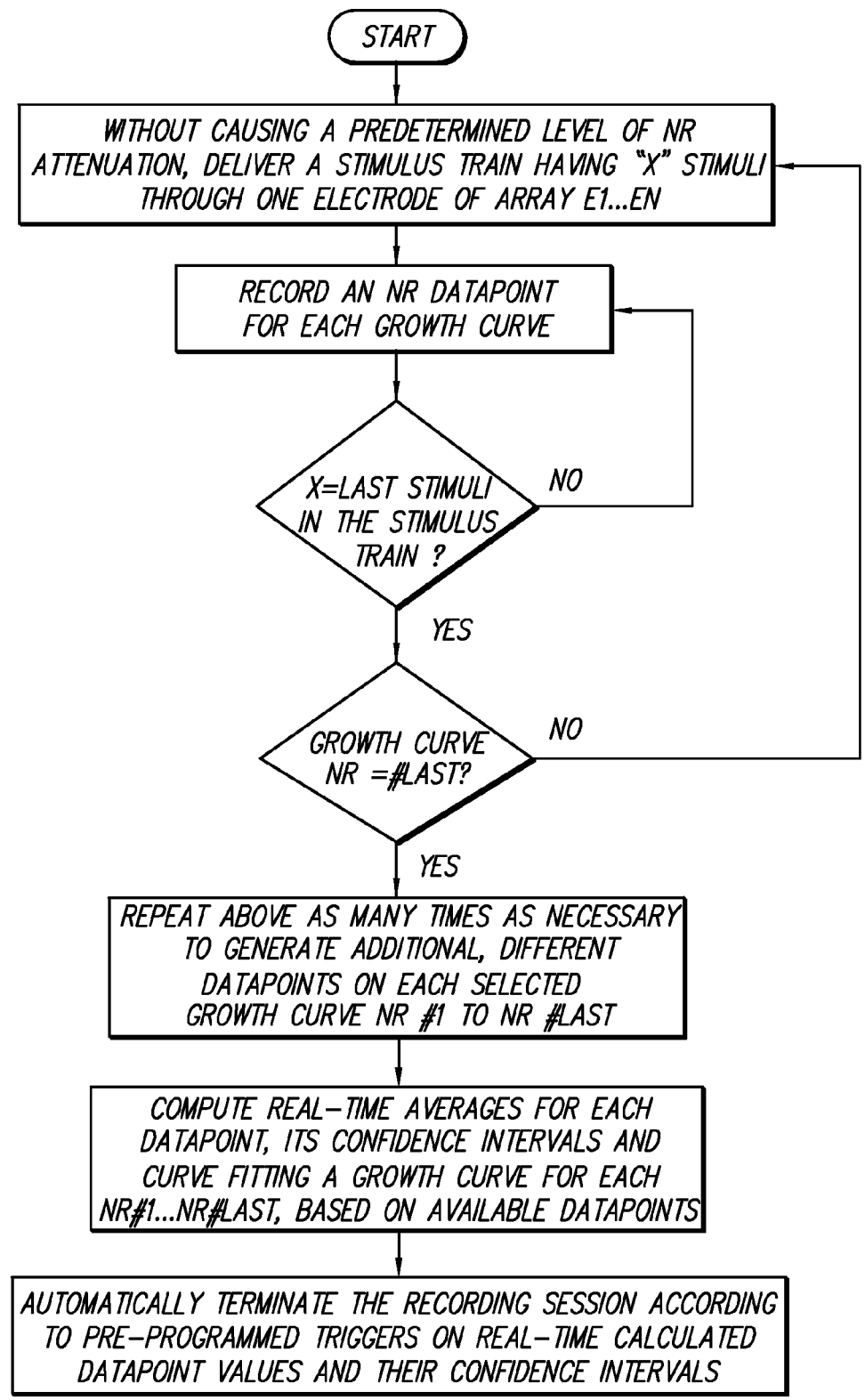
FIG. 7 is forth flow chart of an exemplary method of obtaining neural responses with a stimulation system having an array of electrodes, E1 . . . En, to generate growth curves.
Figure 8:
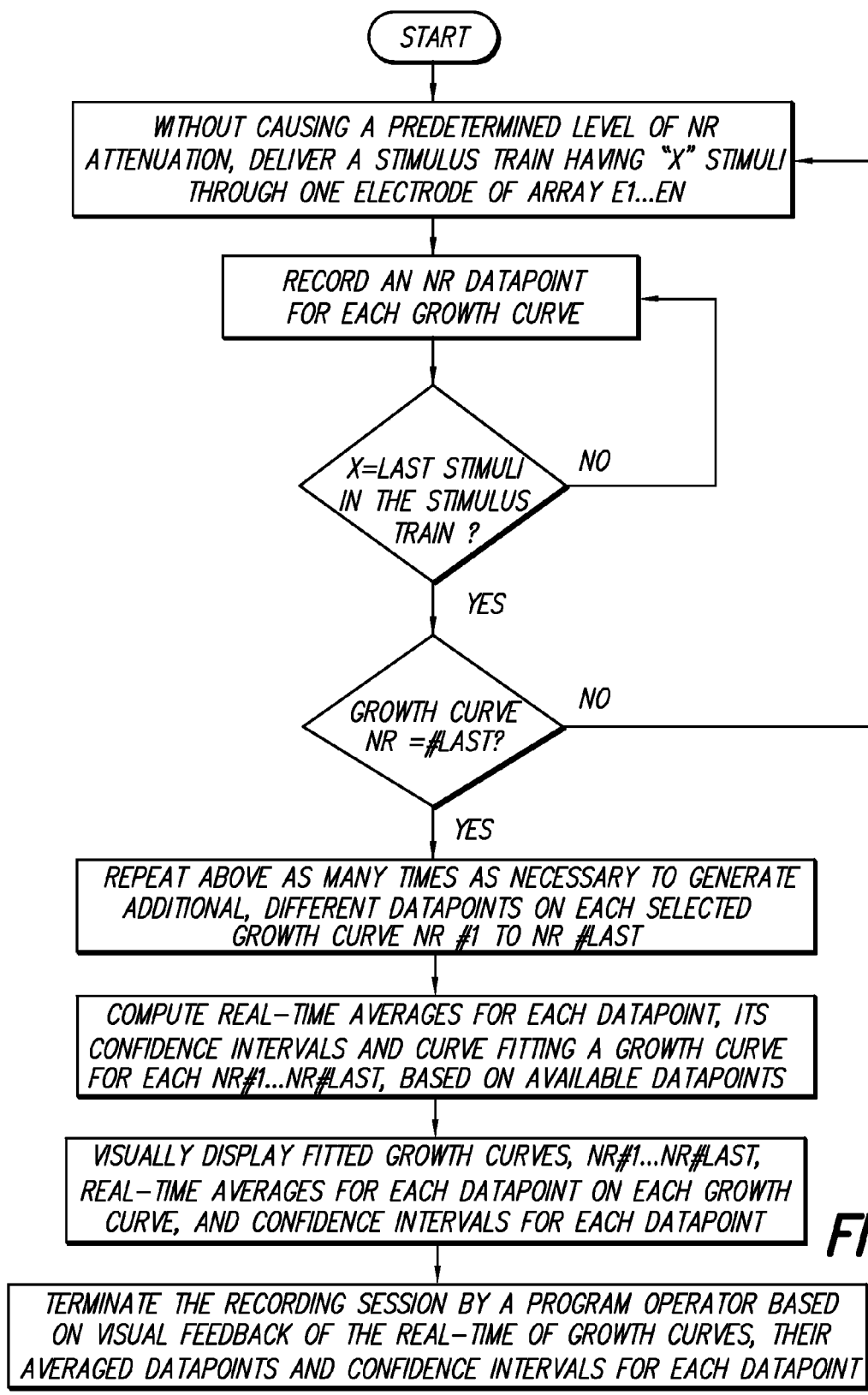
FIG. 8 is fifth flow chart of an exemplary method of obtaining neural responses with a stimulation system having an array of electrodes, E1 . . . En, to generate growth curves.
Figure 9:
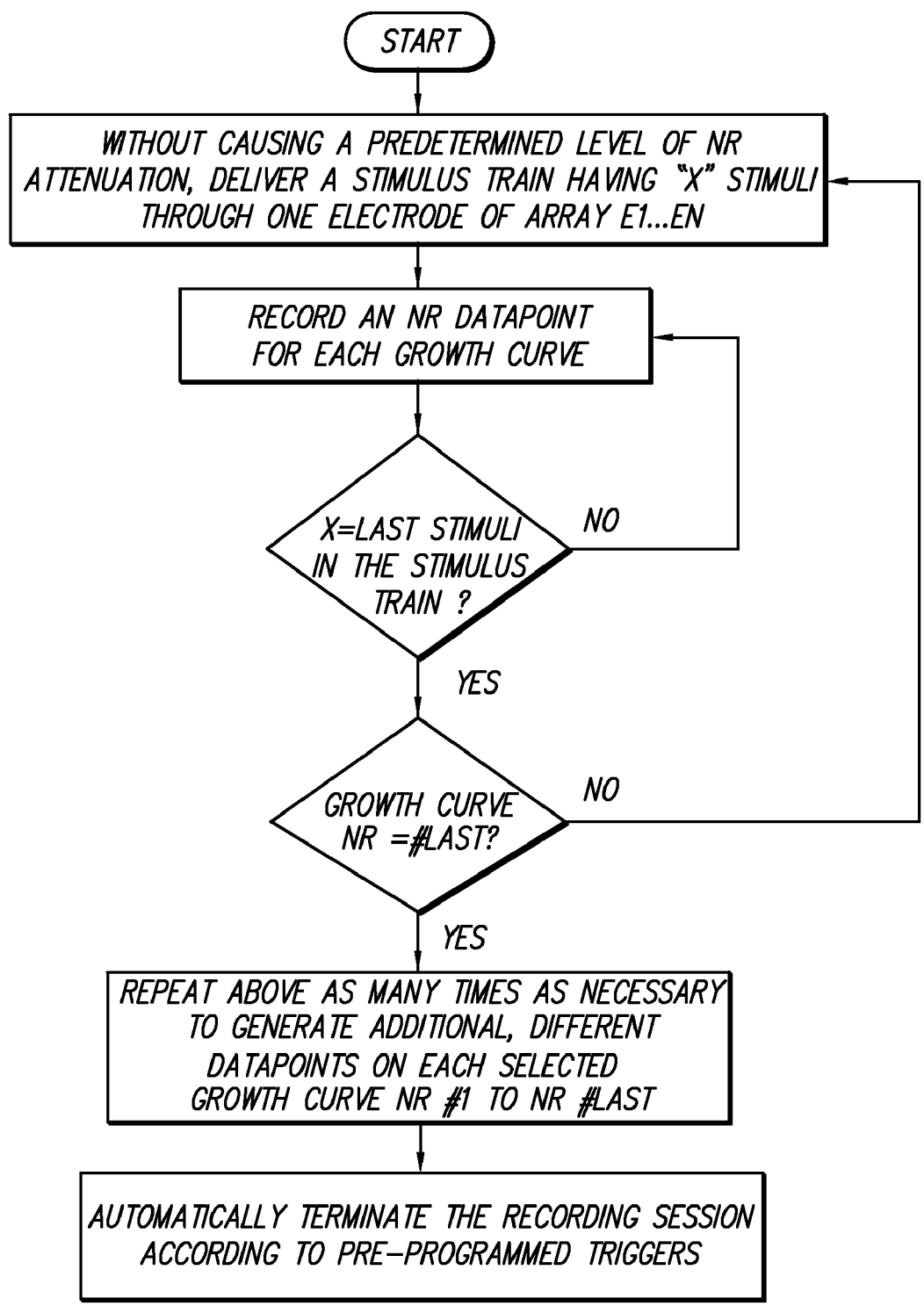
FIG. 9 is sixth flow chart of an exemplary method of obtaining neural responses with a stimulation system having an array of electrodes, E1 . . . En, to generate growth curves.
Figure 10:
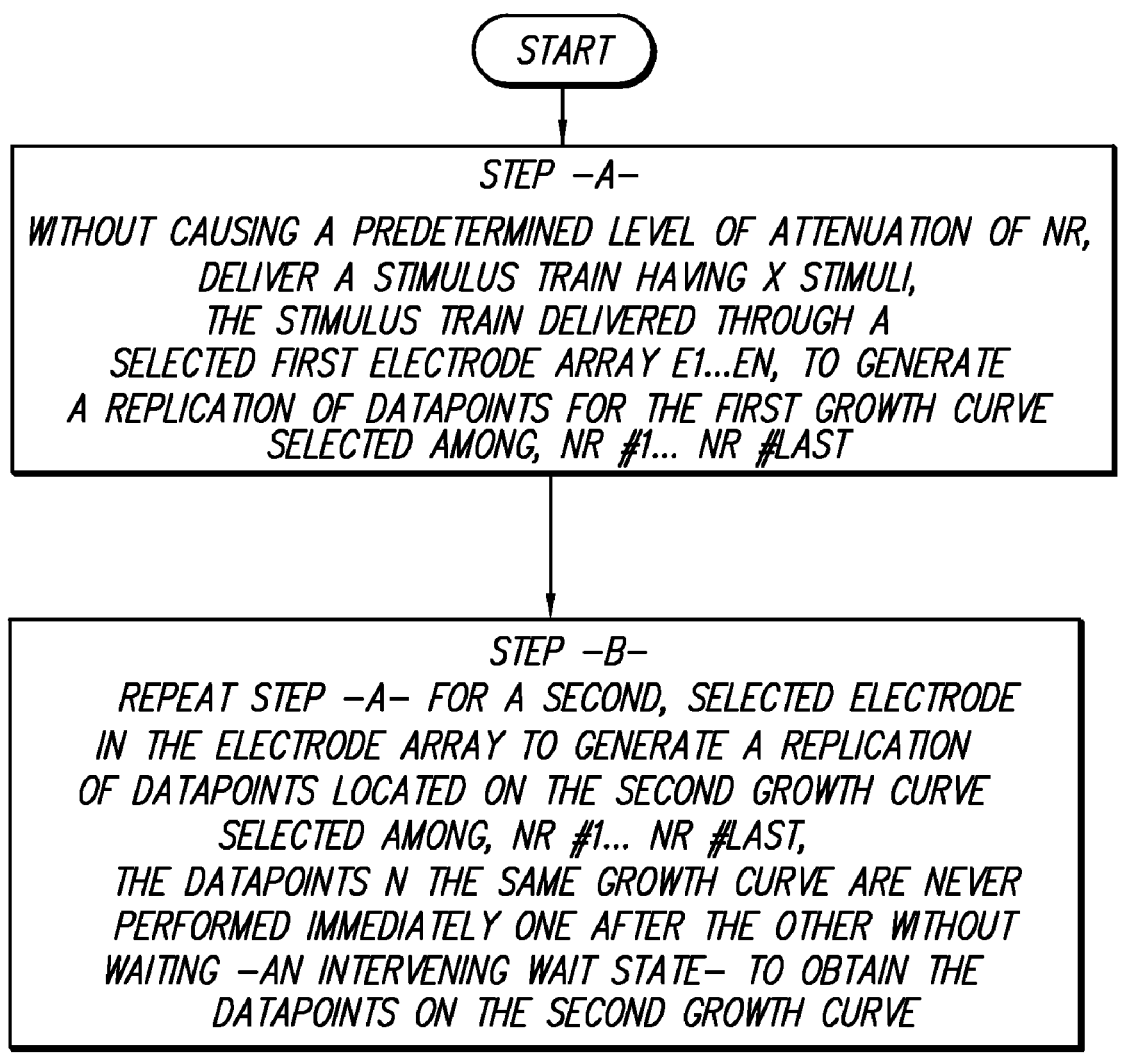
FIG. 10 is a flow chart of an exemplary method of obtaining neural responses to generate at least two growth curves with a stimulation system having an array of stimulating electrodes.

FIG. 3, shows four growth curves, NR #1, NR #2, NR #3 and NR #4 corresponding to sets of target nerves stimulated by unique electrodes or electrode configurations, which may be monopolar, bipolar, or even a configuration having multiple stimulating electrodes. If each electrode is stimulated, for example, in a monopolar mode, e.g., then each electrode, E1 . . . EN, can be selected as a stimulating electrode. NR #1 can represent a growth curve obtained by delivering stimuli through, for example, electrode 10 (E1) (as seen in FIG. 1A); NR #2 can represent a growth curve obtained by delivering stimuli through electrode 11 (E2); NR #3 can represent a growth curve obtained by delivering stimuli through electrode 12, and so on, until NR #4 (or NR #Last) is completed.

It can be seen that each growth curve is obtained by recording and then plotting the resulting multiple datapoints (peak neural responses) as a function of varying applied stimulus amplitude. In the simplest case, which assumes a growth curve that is linear, only two datapoints are necessary to fit a growth curve. In such a case, two points determine a line and the X-zero intercept may be easily calculated. However, typically more datapoints are taken in order to obtain a more accurate picture of growth curves since they are generally not linear.

It can be appreciated that in order to obtain an accurate growth curve for a particular electrode configuration, it is usually necessary to obtain multiple recordings for each datapoint. This is necessary because individual recorded action potentials obtained are ragged and not consistent from recording to recording. Multiple recordings are usually needed to utilize processing strategies to remove the stimulus artifact and also to improve the accuracy of the recorded action potential. If more recordings of datapoints are obtained, the curve fitting will be more accurate. On the other hand, the trade-off is that more time will be taken to complete a recording session.

Modern stimulating systems permit a large number of electrodes and electrode configurations to be used and the stimulus from these electrodes can be independently controlled in order to "steer" the stimulating current to a specific subset of nerves. U.S. Pat. Nos. 6,393,325 and 6,052,624 disclose the concept of "current steering" using electrode arrays. Both patents are herein incorporated by reference in their entireties. With more stimulating channels or electrode configurations available, more time will be needed to obtain the NR recordings necessary to extrapolate each of the growth curves. The elapsed recording time in a clinical setting can be significant; obtaining a single growth curve may take up to 1 to 5 minutes. If there are sixteen electrode configurations, which is a minimum number in many cochlear applications, the total time to obtain and process the necessary recordings may well exceed an hour. It is apparent that any reduction in time to obtain these recordings would be welcomed by the patient and the clinician.

Conventional recording and processing techniques for obtaining growth curves suffer from inaccuracy because of response adaptation to high frequency stimulation. Often, in order to obtain a single, useful datapoint, multiple numbers of recordings of that datapoint, up to 128 times, are obtained. The usual procedure is to provide repeated applications of an identical stimulus, i.e, a stimulus train, in order to record multiple numbers of the same action potential, which represents an NR datapoint. Unfortunately, the rapid and repeated stimulation of the same set of nerves can cause them to adapt to the stimulation and thereby introduce inaccuracy in obtaining a value for the datapoint. Generally, when adaptation occurs, the response peak of the action potential attenuates or decreases in amplitude as compared to a base stimulation threshold before adaptation has occurred. It can be appreciated that the onset of adaptation is hastened by increasing the frequency of stimulation to the same set of nerves. Thus, on the one hand, it is desired to increase the rapidity of stimulation frequency to obtain the recordings as quickly as possible and to shorten the overall length of the recording session. On the other hand, increasing the rapidity of recordings can worsen the accuracy of the recordings.

The present invention provides a method of recording a multiple number of growth curves, NR#1 . . . NR #Last, using an array of electrodes E1 . . . EN more quickly than presently practiced, while reducing the effect of adaptation, thereby improving accuracy. The method can be summarized briefly as recording NRs using a stimulating sequence such that no nerve or set of nerves, which corresponds to a single growth curve, is successively stimulated beyond a particular number of times, unless a significant intervening wait time is allowed to enable nerve recovery or an intervening stimulation of another set of nerves first occurs. In keeping with this rule, no datapoint is successively recorded beyond a particular number of times, X, which causes unwanted NR attenuation and each nerve set is allowed the maximum possible time for recovery. The value of X can be a whole number 1 or greater. Preferably the value of X is a whole number from 1 to 500. More preferably the value of X is a whole number from 1 to 50.

Thus, a primary rule, in accordance with the present invention, is that after a datapoint has been recorded X number of times (stimulus train), it is not followed immediately by a recording of the same or different datapoint that is on the same growth curve. X is a whole number 1 or greater. In the case where X is equal to one the stimulus train reduces to a single stimulus. As used herein, when the term "stimulus train" is used, it will be inclusive of the case of a single stimulus, i.e., when X=1. After a stimulus train has been delivered through any electrode or electrode configuration, no further delivery of a stimulus occurs should occur through that same any electrode or electrode configuration (and hence to the same nerve or set of nerves) until a sufficient intervening wait time for nerve recovery has passed, either by waiting in a wait state, or using the recovery time to stimulate a second set of nerves. This allows the first set of just stimulated nerves to recover.

To illustrate the application of the method, one does not obtain X successive number of recordings of a first datapoint on NR #1 and then immediately record a second datapoint on NR#1, as that would cause the same set of nerves to be stimulated too many times, too quickly, causing substantial, unwanted attenuation of the NR. By "unwanted attenuation" it is meant a predetermined decrease in the peak NR amplitude, e.g., such as a percentage P reduction in the peak. P may be predetermined for example as 2%, 3%, %5 or any other selected value.

Each nerve set is characterized by a specific number of times, X, that the nerve set may be successively stimulated before unwanted attenuation of the NR will occurs. "X", which is a whole number 1 or greater, represents the predetermined, successive number of times a stimulus may be delivered through a particular electrode or electrode configuration to stimulate a particular nerve set, before attenuation of the next, (X+1)th NR reaches a preselected, set percentage decrease, P, of the NR peak amplitude, e.g., the first NR recorded. For example, a trigger percentage P may be preselected as a 5% decrease in a previously recorded peak NR. The variable, whole number value, X, which preferably is from 1 to 500, is also dependent on the time interval between successive applied stimulus pulses (stimulus train) or the "interpulse interval". The value of X also depends on the electrode type used, the electrode configuration, stimulus pulsewidth and amplitude and the particular response characteristic of the target nerve or nerves. The interpulse interval between successive pulses in a stimulus train is preferably between about 0.002 and 1 second.

Thus, for a particular electrical stimulus having a specific amplitude and pulsewidth, there will be a variable, whole number, X, which represents the successive number of identical stimulus pulses that may be applied before the (X+1)th stimulus will cause an attenuation by a predetermined percentage P.

When there are many electrode configurations, it is advisable to have a recording sequence in which each nerve set that is stimulated is allowed to rest for the maximum allowable time. Thus, if there are sixteen electrodes E1 . . . E16, operating in a monopolar mode, and E1 is the first electrode to deliver stimulation, it is preferable that E1 does not again deliver a stimulus until all fifteen other electrodes have first delivered stimulation. Such a strategy provides the maximum recovery time for a just stimulated nerve or nerve set.

In addition, in an embodiment of the present invention, adjacent electrodes or electrode configurations which may stimulate at least a few of the same nerves, should not be stimulated one after the other, if possible. In other words, when E1 delivers X1 successive number of stimulus pulses followed immediately by delivery of stimulus at E2, because E2 is adjacent to E1, a few of the same nerves may be stimulated again too quickly because of stimulation overlap of nerve coverage between the adjacent electrodes. To avoid this potential cross-talk, it is preferable that the sequence of stimulation be chosen that either eliminates or minimizes this possibility of coverage overlap.

FIGS. 4-10 are flowcharts which illustrate exemplary methods of obtaining neural responses with a stimulation system having an electrode array of electrodes, E1 . . . EN, to generate growth curves, NR#1 to NR #LAST, as described above. Such exemplary methods reduce the inaccuracy of the recordings caused by nerve adaptation to repeated exposure of stimuli. Some examples of recording sequences in accordance with the method of the present invention are provided.

EXAMPLE 1

In a case with four NR curves, in a first recording pass, one datapoint can be recorded from each growth curve. A possible recording sequence is: Datapoint #3 in NR #1 (X=15), Datapoint #1 in NR #2 (X=10), Datapoint #10 in NR #3 (X=12) and Datapoint #3 in NR#4 (X=7). This can continue with Datapoint #12 in NR #1 (X=1), Datapoint #3 in NR #2 (X=20), Datapoint #5 in NR #3 (X=25) and Datapoint #7 in NR#4 (X=9). This recording process can continue until all desired datapoints are collected for each growth curve and an averaged datapoint can be calculated for each datapoint obtained a multiple (variable X) number of times.

In order to obtain different datapoints on a single growth curve, the stimulus magnitude can be varied and the NR recorded. The stimulus magnitude may be varied by varying the current amplitude, while holding the stimulus pulsewidth constant. Another alternative is to hold the amplitude constant while varying the pulsewidth. Or still yet, both parameters may be varied.

By applying stimulus having different magnitudes, it is possible to record NRs for each growth curve, until each datapoint on each growth curve is recorded a multiple number of times. When this is done, a more accurate averaged datapoint can be calculated and a curve can be fitted through each datapoint to yield a particular growth curve.

It is emphasized that it is not necessary to record NRs in an orderly numbered sequence, i.e, NR#1, NR#2, NR#3, and NR#4. Datapoints may be recorded in a random sequence, e.g., NR#3, NR#2, NR#1, and NR#4 or NR#2, NR#4, NR#1, and NR#3.

EXAMPLE 2

As an example of a recording sequence which does not stimulate adjacent electrodes or electrode configurations, in an eight electrode system, as shown in FIG. 1A, a possible stimulation sequence might be: E1 (X1 times), E4 (X2 times), E7 (X3 times), E5 (X4 times), E2 (X5 times), E8 (X6 times), and E3 (X7 times) and E6 (X8 times), where X1, X2 . . . X8 represent different whole numbers 1 or greater. Preferably X1, X2 . . . X8 (which represent variable values of X) is a whole number 1 to 500, and more preferably a whole number 1 to about 50. The variable X's are dependent on a particular stimulus applied, the electrode delivering the stimulus, and the predetermined level of attenuation that can act as a trigger to end stimulation. Repeating this same sequence with different applied stimulus amplitudes results in additional datapoints, one for each growth curve, NR #1 through NR #8. This recording process can be repeated until each growth curve has enough datapoints to allow sufficient curve fitting for each growth curve.

For a five electrode system, a possible sequence is E1, E3, E5, E2, E4, and the same sequence can be repeated as necessary. For a four electrode system a possible sequence is E3, E1, E4 and E2, and same sequence can be repeated as necessary. For a system of three electrodes and below, it is not possible to employ a specific sequence to eliminate adjacent channel cross-talk. It is, however, possible to have a wait state, wherein a specific duration of wait time sufficient for nerve recovery intervenes before stimulation resumes. For example, in a three electrode system, the following stimulation sequence is possible: E1, E3, wait, E2, wait, E1, E3, wait, E2, wait, E1, E3, etc.

EXAMPLE 3

FIG. 3 provides alphabetic labels for each datapoint for four separate electrode configurations, represented by growth curves NR #1, NR #2, NR #3 and NR #4. Each growth curve has four datapoints, from which each respective growth curve can be fitted. X, which is the whole number 1 or greater, represents the number of times an identical stimulus can be applied to obtain one datapoint before unwanted NR attenuation occurs. In a first pass, a datapoint in NR #1 is recorded X1 successive number of times. Then a datapoint in NR#2 is recorded X2 successive number of times, a datapoint in NR #3 is recorded X3 successive number of times and a datapoint in NR #4 is recorded X4 number times, where X1, X2, X3 and X4 represent the specific variable values of X's (whole numbers 1 or greater) for each datapoint.

One possible sequence for obtaining all the data points for NR #1, NR #2, NR #3 and NR #4 (shown in FIG. 3) is L, A, N, G, wait, K, D, P, E, wait, I, C, M, H, wait, J, B, O, F. "Wait", as used here, signifies that a short period of time that may optionally be taken before proceeding to a subsequent recording. It can be seen that the wait period can help reduce stimulus adaptation in a nerve because otherwise, adjacent electrodes are stimulated immediately one after the other, which may cause the same set of nerves to be stimulated too often.

This same sequence of recordings may be repeated multiple times, for example, so that more of the same datapoints are obtained. It is emphasized, in a first recording pass, that each datapoint, L, A, N, G, K, D, P, E, I, C. M, H, J, B, O, F, is recorded a multiple number of times in response to a stimulus train at each datapoint. Repeating the entire sequence can provide additional datapoints, if necesssary, to obtain a more accurate average.

EXAMPLE 4

In another example, X may be chosen as constant whole number 1 or greater. That is, X is the same whole number value for every datapoint. In that case, X, must be chosen so as to prevent a particular level of attenuation for every datapoint after successively stimulating X number of times, i.e, with a stimulus train.

The stimulus delivered may be monopolar, e.g., stimulus S1 is delivered through electrode E1, stimulus S2 is delivered through electrode E2, stimulus S3 is delivered through electrode E3 and stimulus S4 is delivered through electrode E4. Each of the stimulus S1, S2, S3 and S4 may be of different magnitudes (energy levels) or they may be the same magnitudes. The NRs may be obtained by stimulating through the electrodes out of sequence, e.g., E3, E4, E1 and E2.

In a further embodiment of the present invention, it may be possible to reduce the absolute number of recordings made by terminating the recording session early. For instance, as each iteration of recordings is obtained, e.g., a first set of averaged datapoints, L, A, N, G, K, D, P, E, I, C, M, H, J, B, O, and F, can be followed, if necessary, by a second set of averaged datapoints L, A, N, G, K, D, P, E, I, C, M, H, J, B, O, and F, followed, if necessary, by a third set of averaged data points L, A, N, G, K, D, P, E, I, C, M, H, J, B, O, and F, etc., real-time calculations can be performed to provide an averaged value for the peak of each datapoint. Using statistical methods, the confidence intervals, e.g., standard deviation, associated with each data point can be immediately calculated. A "smart" software program may be devised where, as the confidence intervals tighten up for each datapoint of the same growth curve, the software program will determine that no further recordings are necessary for that particular datapoint or, for that matter, any other datapoint on that growth curve. It is, of course, necessary to program specific triggering criteria upon which the software would terminate the recording of a specific datapoint, or of a growth curve.

Alternatively, the datapoints may be visually displayed real-time, for example, on a computer screen or another type of display which updates the precise location of the averaged datapoints of each, separate NR curves, as shown in FIG. 3, which datapoints can also have circles, ovals, vertical and horizontal error bars, or other indications of confidence intervals around the presently calculated, real-time value of the averaged datapoint. In addition, each growth curve fitted to the available datapoints can also be displayed in real-time.

Optionally, the operator or clinician may stop the recording of a particular datapoint or a particular NR growth curve (or the recording session) when it is visually clear that the tightness of the confidence intervals around a datapoint displayed on the screen is not changing appreciably or when there is no further discernible relative movement of the growth curve. In such a way, the clinician may optionally terminate the recordings early without having to run through a full set of recordings for a growth curve. Thus, instead of completing 128 recordings scheduled for each datapoint, it may be sufficient only to complete a fraction of these recordings in light of the real-time calculated confidence intervals and also in light of the status of the other datapoints on the same growth curve and their respective confidence intervals. Consequently, by eliminating the acquisition of unnecessary recordings, the time required for an overall recording session can be significantly reduced.

If electrode modes other than monopolar configuration are used, for example, a multiple electrode configuration, the same primary rule applies. To reiterate, the primary rule followed in accordance with the present method is that after stimulation X times (where X is a whole number 1 or greater) with the same electrode or electrode configuration, that should not be followed immediately by stimulation again with the same electrode or electrode configuration. Or, in other words, the same set of nerves should not be stimulated more than X times without a resting or "wait time" sufficient for nerve recovery, during which wait time, it is best to stimulate another set of nerves through a different electrode or electrode configuration.

In accordance with the present invention, another general rule that may be applied is that when adjacent electrodes or electrode configurations can stimulate a subset of the same nerves, if possible, preclude the stimulation of adjacent electrodes or electrode configurations in immediate succession, i.e, one after the other, unless there is sufficient intervening wait time. If there is cross-talk between electrode configurations (channels), the recording sequence should therefore be adjusted to prevent or, at least, minimize stimulating the adjacent channels or electrode configurations immediately one after the other.

In sum, the present invention is advantageous over the conventional method of acquiring NR curves for various electrode configurations. First, the neural response curves obtained will be more accurate because the effect of stimulus adaptation will be reduced. Second, because the recordings are more accurate, it may be possible to do fewer recordings to more quickly reach the desired confidence levels for each datapoint. Furthermore, the present invention allows the use of a smart software program which can detect when further recordings of a particular datapoint can be discontinued based on the real-time calculated confidence levels of a particular datapoint, as well as its relation to the real-time calculated confidence levels of other datapoints for the same growth curve. Alternatively, an operator may discontinue a recording or a recording session early based on real-time recording data. The total time necessary to complete a recording session can thereby be significantly reduced.

While the invention herein disclosed has been described by means of specific embodiments and applications thereof, numerous modifications and variations could be made thereto by those skilled in the art without departing from the scope of the invention set forth in the claims.

What is claimed is:

1. A method of obtaining neural responses (NR) with a stimulation system having an array of electrodes, E1 ... EN, to generate growth curves, NR #1 to NR #Last, the method comprising:
    (a) delivering, without causing a predetermined level of NR attenuation, a stimulus train having X stimuli through one electrode of the array E1 ... EN and recording, X number of times, a first NR datapoint, which datapoint is part of growth curve NR #1;
    (b) repeating the above process of stimulating through each selected ones of electrodes of the array E1 ... EN and recording a datapoint corresponding to each selected electrode and each growth curve, NR #2 to NR #Last, wherein each datapoint is recorded at least once, without causing a predetermined level of NR attenuation; and
    (c) repeating the above steps (a) and (b) as many times as necessary to generate additional, different datapoints on each selected growth curve NR#1 to NR #Last;
    wherein X is a variable, whole number 1 or greater, and X represents the number of stimuli in any stimulus train; and
    wherein no two adjacent electrodes or electrode configurations deliver stimulation immediately, one after the other, in order to reduce channel cross-talk.

2. The method of claim 1, wherein the step (c) to generate additional, different datapoints on each NR growth curve from NR#1 to NR #Last is accomplished by varying the stimulus amplitude while keeping the stimulus pulsewidth constant.

3. The method of claim 1, further comprising:
    (d) obtaining an averaged datapoint for each growth curve NR#1 to NR #Last by averaging all available recordings for each datapoint.

4. The method of claim 1, further comprising:
    (d) computing real-time averages of each datapoint, its confidence intervals and curve fitting a growth curve for each NR #1 ... NR #Last, based on available datapoints.

5. The method of claim 4, further comprising:
    (e) automatically terminating the recording session according to pre-programmed triggers based on real-time calculated datapoint values and their confidence intervals.

6. The method of claim 4, further comprising:
    (e) visually displaying fitted growth curves, NR #1 ... NR #Last, real-time averages of each datapoint on each growth curve, and confidence intervals for each datapoint; and
    (f) terminating the recording session by a program operator based on visual feedback of the real-time display of growth curves, their averaged datapoints and confidence intervals for each datapoint.

7. The method of claim 1, further comprising:
(d) automatically terminating the recording of a current datapoint by a software program based on pre-programmed triggers.

8. The method of claim 1, wherein the electrodes stimulate spinal cord nerves.

9. The method of claim 1, wherein the electrodes stimulate cochlear nerves.

10. The method of claim 9, wherein X is a variable, whole number between 1 and 50.

11. The method of claim 9, wherein the inter-stimulus time interval between the delivery of successive stimuli for successively recording one datapoint is between about 0.002 and 1 second.

12. A method of obtaining neural responses to generate at least two growth curves with a stimulation system having an array of stimulating electrodes, E1 . . . EN, the method comprising:
(a) delivering a stimulus train having X stimuli, without causing a predetermined level of attenuation of NR, the stimulus train delivered through a selected first electrode in the electrode array E1 . . . EN, to generate a replication of a data point for the first growth curve selected among, NR #1 . . . NR #Last; and
(b) repeating step (a) for at least a second, selected electrode in the electrode array to generate a replication of a datapoint located on at least a second growth curve selected among, NR#1 . . . NR #Last,
wherein delivering a first stimulus train to obtain a first datapoint and delivering a second stimulus train to obtain a second datapoint, when the two datapoints are located on the same, first growth curve, are never performed immediately one after the other, without the occurrence of an intervening wait state or an intervening delivery of a third stimulus to obtain a datapoint on a different, second growth curve;
wherein X is a variable, whole number 1 or greater; and
wherein the predetermined level of attenuation of the NR is a decrease of the last NR, in response to the (X+1)th stimulus, by at least a predetermined percentage, P.

13. The method of claim 12, further comprising:
(c) repeating, multiple times, the steps (a) and (b), by applying stimuli having different magnitudes when applying a stimulus train through each selected electrode, to obtain additional replications of datapoints in order to generate selected growth curves, NR#1 . . . NR #Last.

14. The method of claim 12, wherein the growth curves are for cochlear nerves.

15. The method of claim 14, wherein each stimulus train has between 1 and 50 substantially identical stimulus pulses.

16. The method of claim 15, wherein the inter-stimulus time interval between successive stimuli in each stimulus train is between about 1 to 0.002 seconds.

17. The method of claim 12, wherein stimulation is accomplished with a monopolar electrode configuration.

18. A method of obtaining neural responses to generate at least two growth curves with a stimulation system having an array of stimulating electrodes, E1 . . . EN, the method comprising:
(a) delivering a stimulus train having X stimuli, without causing a predetermined level of attenuation of NR, the stimulus train delivered through a selected first electrode in the electrode array E1 . . . EN, to generate a replication of a data point for the first growth curve selected among, NR #1 . . . NR #Last; and
(b) repeating step (a) for at least a second, selected electrode in the electrode array to generate a replication of a datapoint located on at least a second growth curve selected among, NR#1 . . . NR #Last;
wherein delivering a first stimulus train to obtain a first datapoint and delivering a second stimulus train to obtain a second datapoint, when the two datapoints are located on the same, first growth curve, are never performed immediately one after the other, without the occurrence of an intervening wait state or an intervening delivery of a third stimulus to obtain a datapoint on a different, second growth curve;
wherein X is a variable, whole number 1 or greater; and
wherein, when there are first and second adjacent electrodes having overlapping coverage of a subset of nerves and a first stimulus train is delivered through the first electrode, a second stimulus train is not immediately thereafter, delivered through the second, adjacent electrode, without an occurrence of an intervening wait time sufficient for nerve recovery of nerves stimulated by the first stimulus train or a delivery of a third stimulus train to a third electrode, which third electrode is not adjacent to the first electrode.

19. The method of claim 18, further comprising:
(c) repeating, multiple times, the steps (a) and (b), by applying stimuli having different magnitudes when applying a stimulus train through each selected electrode, to obtain additional replications of datapoints in order to generate selected growth curves, NR#1 . . . NR #Last.

20. The method of claim 18, wherein the growth curves are for cochlear nerves.

21. The method of claim 20, wherein each stimulus train has between 1 and 50 substantially identical stimulus pulses.

22. The method of claim 21, wherein the inter-stimulus time interval between successive stimuli in each stimulus train is between about 1 to 0.002 seconds.

23. The method of claim 18, wherein stimulation is accomplished with a monopolar electrode configuration.

24. A method of obtaining neural responses with a stimulation system having an array of electrodes, E1 . . . EN, to generate growth curves, NR #1 to NR #Last, the method comprising:
(a) delivering, without causing a predetermined level of NR attenuation, a stimulus train having X stimuli through one electrode of the array E1 . . . EN and recording, X number of times, a first NR datapoint, which datapoint is part of growth curve NR #1;
(b) repeating the above process of stimulating through each selected ones of electrodes of the array E1 . . . EN and recording a datapoint corresponding to each selected electrode and each growth curve, NR #2 to NR #Last, wherein each datapoint is recorded at least once, without causing a predetermined level of NR attenuation;
(c) repeating the above steps (a) and (b) as many times as necessary to generate additional, different datapoints on each selected growth curve NR#1 to NR #Last; and
(d) obtaining an averaged datapoint for each growth curve NR#1 to NR #Last by averaging all available recordings for each datapoint;
wherein X is a variable, whole number 1 or greater, and X represents the number of stimuli in any stimulus train.

25. The method of claim 24, wherein the step (C) to generate additional, different datapoints on each NR growth curve from NR#1 to NR #Last is accomplished by varying the stimulus amplitude while keeping the stimulus pulse-width constant.

26. A method of obtaining neural responses with a stimulation system having an array of electrodes, E1 . . . EN, to generate growth curves, NR #1 to NR #Last, the method comprising:

(a) delivering, without causing a predetermined level of NR attenuation, a stimulus train having X stimuli through one electrode of the array E1 . . . EN and recording, X number of times, a first NR datapoint, which datapoint is part of growth curve NR #1;

(b) repeating the above process of stimulating through each selected ones of electrodes of the array E1 . . . EN and recording a datapoint corresponding to each selected electrode and each growth curve, NR #2 to NR #Last, wherein each datapoint is recorded at least once, without causing a predetermined level of NR attenuation;

(c) repeating the above steps (a) and (b) as many times as necessary to generate additional, different datapoints on each selected growth curve NR#1 to NR #Last; and (d) computing real-time averages of each datapoint, its confidence intervals and curve fitting a growth curve for each NR #1 . . . NR #Last, based on available datapoints;

wherein X is a variable, whole number 1 or greater, and X represents the number of stimuli in any stimulus train.

27. The method of claim 26, wherein the step (c) to generate additional, different datapoints on each NR growth curve from NR#1 to NR #Last is accomplished by varying the stimulus amplitude while keeping the stimulus pulsewidth constant.

28. A method of obtaining neural responses with a stimulation system having an array of electrodes, E1 . . . EN, to generate growth curves, NR #1 to NR #Last, the method comprising:

(a) delivering, without causing a predetermined level of NR attenuation, a stimulus train having X stimuli through one electrode of the array E1 . . . EN and recording, X number of times, a first NR datapoint, which datapoint is part of growth curve NR #1;

(b) repeating the above process of stimulating through each selected ones of electrodes of the array E1 . . . EN and recording a datapoint corresponding to each selected electrode and each growth curve, NR #2 to NR #Last, wherein each datapoint is recorded at least once, without causing a predetermined level of NR attenuation;

(c) repeating the above steps (a) and (b) as many times as necessary to generate additional, different datapoints on each selected growth curve NR#1 to NR #Last;

(d) computing real-time averages of each datapoint, its confidence intervals and curve fitting a growth curve for each NR #1 . . . NR #Last, based on available datapoints; and (e) automatically terminating the recording session according to pre-programmed triggers based on real-time calculated datapoint values and their confidence intervals;

wherein X is a variable, whole number 1 or greater, and X represents the number of stimuli in any stimulus train.

29. The method of claim 28, wherein the step (c) to generate additional, different datapoints on each NR growth curve from NR#1 to NR #Last is accomplished by varying the stimulus amplitude while keeping the stimulus pulsewidth constant.

30. A method of obtaining neural responses with a stimulation system having an array of electrodes, E1 . . . EN, to generate growth curves, NR #1 to NR #Last, the method comprising:

(a) delivering, without causing a predetermined level of NR attenuation, a stimulus train having X stimuli through one electrode of the array E1 . . . EN and recording, X number of times, a first NR datapoint, which datapoint is part of growth curve NR #1;

(b) repeating the above process of stimulating through each selected ones of electrodes of the array E1 . . . EN and recording a datapoint corresponding to each selected electrode and each growth curve, NR #2 to NR #Last, wherein each datapoint is recorded at least once, without causing a predetermined level of NR attenuation;

(c) repeating the above steps (a) and (b) as many times as necessary to generate additional, different datapoints on each selected growth curve NR#1 to NR #Last;

(d) computing real-time averages of each datapoint, its confidence intervals and curve fitting a growth curve for each NR #1 . . . NR #Last, based on available datapoints;

(e) visually displaying fitted growth curves, NR #1 . . . NR #Last, real-time averages of each datapoint on each growth curve, and confidence intervals for each datapoint; and (f) terminating the recording session by a program operator based on visual feedback of the real-time display of growth curves, their averaged datapoints and confidence intervals for each datapoint;

wherein X is a variable, whole number 1 or greater, and X represents the number of stimuli in any stimulus train.

31. The method of claim 30, wherein the step (c) to generate additional, different datapoints on each NR growth curve from NR#1 to NR #Last is accomplished by varying the stimulus amplitude while keeping the stimulus pulsewidth constant.

32. A method of obtaining neural responses with a stimulation system having an array of electrodes, E1 . . . EN, to generate growth curves, NR #1 to NR #Last, the method comprising:

(a) delivering, without causing a predetermined level of NR attenuation, a stimulus train having X stimuli through one electrode of the array E1 . . . EN and recording, X number of times, a first NR datapoint, which datapoint is part of growth curve NR #1;

(b) repeating the above process of stimulating through each selected ones of electrodes of the array E1 . . . EN and recording a datapoint corresponding to each selected electrode and each growth curve, NR #2 to NR #Last, wherein each datapoint is recorded at least once, without causing a predetermined level of NR attenuation;

(c) repeating the above steps (a) and (b) as many times as necessary to generate additional, different datapoints on each selected growth curve NR#1 to NR #Last; and (d) automatically terminating the recording of a current datapoint by a software program based on pre-programmed triggers;

wherein X is a variable, whole number 1 or greater, and X represents the number of stimuli in any stimulus train.

33. The method of claim 32, wherein the step (C) to generate additional, different datapoints on each NR growth curve from NR#1 to NR #Last is accomplished by varying the stimulus amplitude while keeping the stimulus pulsewidth constant.

* * * * *